(12) United States Patent
Ralph et al.

(10) Patent No.: US 6,916,483 B2
(45) Date of Patent: Jul. 12, 2005

(54) BIOABSORBABLE PLUGS CONTAINING DRUGS

(75) Inventors: James Ralph, Seaside Park, NJ (US); Steve Tatar, Montville, NJ (US)

(73) Assignee: BioDynamics, LLC, Englewood, NJ (US)

( * ) Notice: Subject to any disclaimer, the term of this patent is extended or adjusted under 35 U.S.C. 154(b) by 322 days.

(21) Appl. No.: 10/200,355

(22) Filed: Jul. 22, 2002

(65) Prior Publication Data

US 2004/0013703 A1 Jan. 22, 2004

(51) Int. Cl.[7] ............... A61F 13/00; A61F 2/00; A61F 2/02
(52) U.S. Cl. ............. 424/422; 424/426; 623/23.75; 623/23.76
(58) Field of Search ............... 424/422, 426; 623/23.75, 23.76

(56) References Cited

U.S. PATENT DOCUMENTS 5,681,289 A * 10/1997 Wilcox et al.
6,656,488 B2 * 12/2003 Yi et al.

* cited by examiner

*Primary Examiner*—Thurman K. Page
*Assistant Examiner*—Humera N. Sheikh

(57) ABSTRACT

Bioabsorbable modular drug delivery devices having shapes and sizes adapted to be inserted within a mating receptacle on the surface of an implantable prosthesis are disclosed. The devices may be attached to one another to create custom drug delivery devices having controllable drug release characteristics that depend on the composition of individual modules comprising the device. The modules may be cylinders, disks, tiles or tubes comprised of a bioabsorbable polymer and a therapeutic agent. The therapeutic agent(s) may be homogeneously distributed throughout the polymeric body of the device or contained within a cavity within a module comprising the device, or both. The device(s) may be threaded or attached to a prosthesis by a biodegradable adhesive. The modular devices may also be formed into tapered plugs for insertion into a mating receptacle. In another embodiment, the drug delivery device may be inserted within a mesh bag that may be attached to a soft tissue as, for example, by sutures, for localized controlled dispensation of a therapeutic agent.

20 Claims, 2 Drawing Sheets

BIOABSORBABLE PLUGS CONTAINING DRUGS

BACKGROUND OF THE INVENTION

1. Field of the Invention

The invention relates to methods and implantable devices for dispensing one or more therapeutic agents at a surgical site. More particularly, the invention relates to devices and methods for controllably delivering therapeutic agents to an orthopaedic surgical site that requires the implantation of a prosthesis within the site.

2. Prior Art

Biodegradable materials are used in medicine for a variety of purposes including drug delivery devices and as aids in tissue repair. The physical and chemical properties of such materials can vary as in the case of different polymeric materials, e.g., melting point, degradation rate, stiffness, etc. The variability in physical and chemical properties of biodegradable polymeric materials allows biodegradable implants made from such materials to be tailored to suit specific applications.

A resorbable bone wax is described in U.S. Pat. No. 5,143,730. The bone wax is asserted to be suitable for mechanical staunching of bleeding and is based on oligomers of glycolic acid and/or lactic acid with monofunctional and/or polyfunctional alcohols and/or corresponding carboxylic acids.

U.S. Pat. Nos. 4,535,485 and 4,536,158 disclose certain implantable porous prostheses for use as bone or other hard tissue replacement which are comprised of polymeric materials. The disclosed prostheses are composed generally of polymeric particles. The particles have an inner core comprised of a first biologically-compatible polymeric material such as polymethylmethacrylate and an outer coating comprised of a second biologically-compatible polymeric material which is hydrophilic, such as polymeric hydroxyethylmethacrylate. The particles may incorporate a radiopaque material to render the particle visible in an X-ray radiograph. The particles may be bonded together to form a unitary structure which can be implanted in the body. Alternatively, a mass of the particles may be implanted in the body in an unbonded, granular form. In either the bonded or the unbonded form, interstices between the implanted particles form pores into which tissue can grow. Thus, the bioabsorbable particles serve as a structural support and guiding matrix for encroaching bone deposits derived from adjacent fresh bone. The hydrophilic coating on the particles facilitates infusion of body fluids into the pores of the implant, which promotes the ingrowth of tissue into the pores of the implant.

Chesterfield et al., in U.S. Pat. No. 5,697,976, disclose a porous bioabsorbable surgical implant material that is prepared by coating particles of bioabsorbable polymer with tissue ingrowth promoter. Typical bioabsorbable polymers include polymers of glycolide, lactide, caprolactone, trimethylene carbonate, dioxanone, and physical and chemical combinations thereof The tissue ingrowth promoter can include calcium hydroxide and/or a hydrophilic coating material. The hydrophilic coating material can be bioabsorbable or non-bioabsorbable. A typical non-bioabsorbable hydrophilic coating material is polyhydroxyethyl methacrylate (PHEMA). The bioabsorbable implant material may also contain a therapeutic agent. Typical therapeutic agents include an antimicrobial agent, dye, growth factors and combinations thereof.

Medical putty for tissue augmentation is described in U.S. Pat. No. 4,595,713 and is alleged by the inventor to be useful in the regeneration of soft and hard connective tissue. As described therein, the implant material is composed of a copolymer of 60–95% epsilon caprolactone and 40–5% lactide. Catalysts used for the copolymer are metallic esters of carboxylic acids. The polymer is said to become moldable at hot water temperatures of about 115–160° F.

Rosenthal et al., in U.S. Pat. No. 5,700,476, disclose implant materials comprising a matrix structure of sponge, at least one substructure and at least one pharmacologically active agent, wherein both the matrix structure and the substructure are formed from bioabsorbable biopolymers. The substructure may, for example, comprise biopolymer films, flakes, fibres or microspheres embedded in the matrix structure of sponge. The pharmacologically active agent may comprise antiseptics, antibiotics and/or analgesics. One or more such therapeutically active agents may be incorporated separately into the matrix and/or the substructure so as to achieve controlled or phasic release of the active agents into the wound.

Grear Britain Patent GB-A-2215209 describes a biodegradable, osteogenic bonegraft substitute comprising: (a) a porous, rigid structure formed from a biodegradable polymer such as polylactic or polyglycolic acid; (b) a chemotactic substance such as hyaluronic acid, fibronectin or collagen dispersed in the interstices of the rigid structure; and (c) a biologically active or therapeutic substance such as bone morphogenic protein evenly distributed throughout the volume of the bone-graft substitute. In use, the material is implanted into a bone defect. The material helps to restore functional architecture and mechanical integrity of the bone, initiate osteogenesis, and maintain the biological processes of bone growth while simultaneously being slowly bioabsorbed by the host organism.

Akalla et al., in U.S. Pat. No. 5,641,502, disclose a moldable biodegradable surgical material made of a bioabsorbable polymer derived from hydroxyacids, lactones, carbonates, etheresters, anhydrides, orthoesters and copolymers, terpolymers and/or blends thereof. The polymer is blended with at least one surface active agent selected from the group consisting of fatty acid ester and poly (oxypropylene)/poly(oxyethylene) block copolymer. In one embodiment, a leaching agent is blended with the above-mentioned surgical material. Methods of making moldable biodegradable surgical material are provided. The surgical material may be used as a moldable bone wax in connection with repair of wounds and is an adaptable aid for any appropriate surgical use, e.g., hemostat, anchor, patch etc.

The porous bioabsorbable implants that have been suggested to date are generally isotropic materials. That is to say, the structure and composition of the materials are uniform in all directions. Any pharmacological therapeutic agents are generally distributed uniformly in the biodegradable carrier materials. This, in turn, means that the active agents are released uniformly into the wound site at a rate determined only by the rate at which the implant material biodegrades and the surface area of the implant. In practice, it would be preferable to have controlled or phased release of active agents. For example, it may be desired to provide an implant having an initial rapid release of the active therapeutic agent(s) to establish a sufficient concentration of those agents at the wound surface, followed by the slower release required to maintain a constant therapeutically effective concentration. Alternatively, it may be desirable to have an initial rapid release of antiseptic followed by slower release of wound healing factors such as cytokines, EGF etc.

In open surgical procedures, it is common to apply an antibiotic, analgesic, growth stimulator, or other chemical agent at the surgical site prior to closing the incision in order to control infection, decrease pain, promote growth, etc. One of the most devastating complications of orthopaedic surgery such as total joint arthroplasty is deep sepsis. Treatment of an infected joint replacement is difficult due to its location, and localized devascularization resulting from this procedure. Current approaches to therapy for deep infections include systemic or parenteral antibiotic regimes, and the use of antibiotic-impregnated acrylic bone cement. Due to the localized devascularization, it is difficult to establish therapeutic levels of an agent in the bone surrounding the implant without exceeding toxic serum concentrations when utilizing systemic or parenteral treatments. The use of antibiotic-containing bone cement results in high local concentrations, while avoiding toxic serum levels, but the antibiotic has been shown to elute in trace quantities for extended periods of time (greater than one year). Residual trace amounts of antibiotics have raised concerns of resistant strain formation. An additional concern regarding adding antibiotics to bone cement is the possible degradation of mechanical properties of the bone cement whose primary function is as a fixation material.

According to the state of the art, it is preferable to establish and maintain therapeutic concentrations of an antibiotic at a surgical site for a period of 7 to 10 days, with no residual antibiotics lingering for extended periods of time. It is also desirable to achieve such relatively high therapeutic concentrations locally without elevating serum concentrations, thereby reducing the danger of systemic toxicity.

U.S. Pat. No. 5,681,289 to Wilcox et al. discloses a dispensing bladder for passing a low volume flow of a liquid chemical agent at an orthopaedic surgical site. The bladder is installed adjacent to or as part of an orthopaedic implant. It is coupled to a tube which receives a supply of liquid chemical such as an antibiotic via an injection port or an implanted or external reservoir and pump. The bladder may be biodegradable so as to avoid the need for extensive surgery to explant it. However, the tube, injection site, pump, and reservoir must be surgically removed. Moreover, it is believed that the delivery of a liquid antibiotic in the femoral canal may degrade the mechanical properties of bone cement on an implant stem.

In view of the limitations of prior art implantable drug delivery devices, it is desirable to provide an implantable drug delivery device in the form of a shaped plug that may be affixed to a prosthesis, thereafter to biodegrade and deliver one or more therapeutic agents contained therein at a controllable rate to the surrounding tissue.

SUMMARY

It is therefore an object of the invention to provide a modular drug delivery device and method for controllably delivering a therapeutic agent to a surgical site, particularly an orthopaedic surgical site into which a prosthesis has been implanted.

It is a further object of the invention to provide a device and a method for attaching the device to an implantable prosthesis, the device thereafter being operable for delivering an antibiotic to an orthopaedic surgical site and wherein the device does not require surgical removal following implantation.

It is yet a further object of the invention to provide a drug delivery device meeting the above objectives of delivering a therapeutic agent to an orthopaedic surgical site which will deliver a therapeutic dose of the therapeutic agent to the surgical site over a predefined dosing period.

In accordance with these objectives which will be discussed in detail below, the bioabsorbable drug delivery devices in accordance with the various embodiments of the present invention include encapsulating the therapeutic agent in a bioabsorbable polymer, or a modular plug containing more than one bioabsorbable polymer, which will yield a controllable release of the therapeutic agent over a predefined dosing period (such as a 7–10 day period), with residual therapeutic agent being thereafter delivered only until the bioabsorable polymer is completely biodegraded. It is preferable that the drug delivery device be in the form of a rigid, preshaped polymeric plug that can be readily affixed to an orthopaedic prosthesis such as a femoral pin or a bone plate. Suitable therapeutic agents include antibiotics, analgesics and lactoferrin, and a suitable bioabsorbable polymer is poly lactide-co-glycolide (PLGA). Those skilled in the art will readily appreciate that other bioabsorable polymers can be substituted for PLGA, for example (without limitation), PLA, etc.

Embodiments of a drug delivery device in accordance with the present invention include modular plugs configured as cylinders, capsules, disks, cylinders comprised of a plurality of stacked disks, a rectangular plaque or tile, a tapered conical plug or a threaded cylindrical plug that may be screwed into a hole drilled within a bone or the rigid body of a prosthesis or disposed within a mesh bag for implantation at a surgical site.

The features of the invention believed to be novel are set forth with particularity in the appended claims. However the invention itself, both as to organization and method of operation, together with further objects and advantages thereof may be best understood by reference to the following description taken in conjunction with the accompanying drawings in which:

DESCRIPTION OF THE PREFERRED EMBODIMENTS

It will be understood by the artisan that the bioabsorbable drug delivery devices discussed hereinbelow may be formed out of polymer blends of glycolide and/or lactide homopolymer, copolymer and/or glycolide/lactide copolymer and polycaprolactone copolymers, and/or copolymers of glycolide, lactide, poly (L-lactide-co-DL-lactide), caprolactone, polyorthoesters, polydioxanone, trimethylene carbonate and/or polyethylene oxide or any other bioabsorbable material. Similarly, it will be further understood that therapeutic agents suitable for timed release by the various embodiments of the drug delivery device described herein include antibiotic compositions, analgesics, lactoferrin and any other compositions effective for reducing infection and/or promoting healing of a wound formed at a surgical site.

As used herein, the term "biodegradable" means that the composition will degrade over time by enzymatic action, by hydrolytic action and/or by other similar mechanisms in the human body. The term "bioabsorbable," means that the composition will be biodegraded and that the products of biodegradation will either be absorbed by tissue within the body or excreted.

Figure 1A:
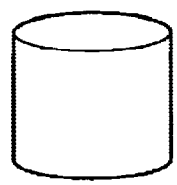
FIGS. 1a–j illustrate various embodiments of bioabsorbable drug delivery plugs in accordance with different configurations of the present invention.
Figure 1B:
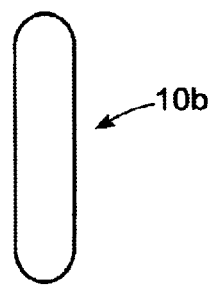
Figure 1C:
Figure 1D:
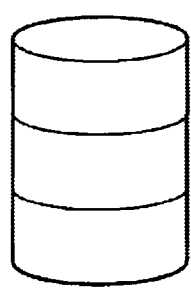
Figure 1E:
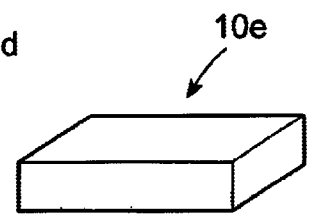
Figure 1F:
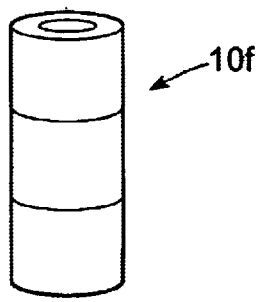
Figure 1G:
Figure 1H:
Figure 1I:
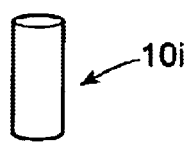
Figure 1J:
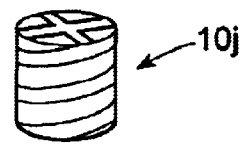

Turning now to FIGS. 1a–j, various implantable modular drug delivery devices (herein after referred to alternatively as "implants" or "devices") in accordance with the present invention are shown in perspective view. All embodiments of the device are designed to fit snugly within a receiving cavity in a prosthesis so as not to alter the profile thereof. Different embodiments 10a–10k of the device can be stacked and adhered together to generate new embodiments. FIG. 1a shows a cylindrical implant 10a comprising a solid cylinder of a biodegradable polymer containing a therapeutic agent distributed substantially homogeneously throughout the volume thereof. The cylindrical device 10a may have a threaded exterior surface and a slotted head, as shown in FIG. 1j, to enable the device 10a to be screwed into a hole tapped in a prosthesis (not shown).

FIG. 1b is a perspective view of a capsular embodiment 10b of the device. The capsular embodiment 10b may be solid or have a hollow interior chamber. Either the interior chamber and/or the biodegradable polymer comprising the capsular material may include a therapeutic agent. FIG. 1c shows a disk embodiment 10c of the device. The disk 10c comprises a biodegradable polymer containing a therapeutic agent distributed substantially homogeneously throughout the volume thereof. Two or more such disks 10c may be stacked, as shown in FIG. 1d, and bonded to one another in the manner indicated in embodiment 10d in FIG. 1d.

Figure 2:
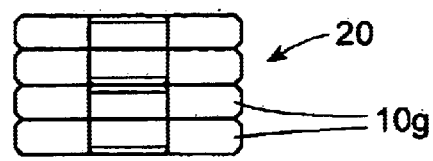
FIG. 2 is a cross-sectional view of an embodiment of a drug delivery device in accordance with the present invention comprising a plurality of stacked annular modules affixed to one another.

FIG. 1e shown a rectangular tile 10e comprised of a biodegradable polymer and a therapeutic agent. The tile embodiment 10e is designed to be received within, and adhered to, a mating receptacle within the flat outer surface of a prosthesis such as a bone plate. FIG. 1f shows a rod embodiment 10f of the device comprising a plurality of cylindrical embodiments 10a of the device stacked end-to-end and bonded to one another in the manner indicated. If the cylinders 10a have an axial bore therewithin (not shown), a tubulatr embodiment (not shown) can be formed. The cylinders 10a comprising the rod embodiment 10f may comprise the same or different therapeutic agents and the same or different biodegradable polymer compositions. Rod embodiment 10f may be inserted within a cylindrical recess in a prosthesis thereafter to sequentially release different therapeutic agents or the same therapeutic agent at different release rates following implantation within the body. FIG. 10g illustrates an "O-ring" embodiment 10g of a modular device. The O-ring embodiment 10g may be stacked as indicated in the "poly O-ring" embodiment 20 of FIG. 2. A tapered plug embodiment 10h of a device in accordance with the present invention is shown in FIG. 1h. A tubular modular embodiment of the device is indicated at 10i in FIG. 1i. FIG. 1j shows a threaded cylindrical embodiment 10j of the device.

Figure 3:
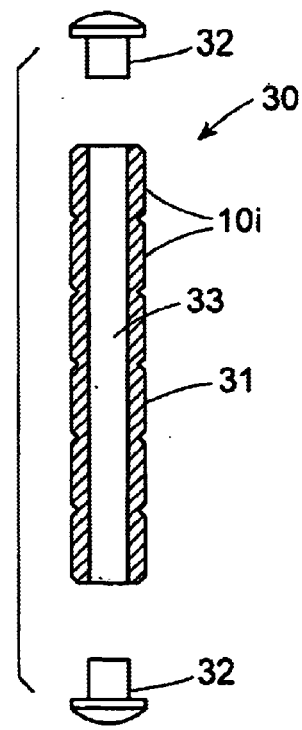
FIG. 3 is a cross-sectional view of an implantable drug delivery device in accordance with yet a further embodiment of the present invention comprising a plurality of stacked tubular modules affixed to one another end-to-end.
Figure 4:
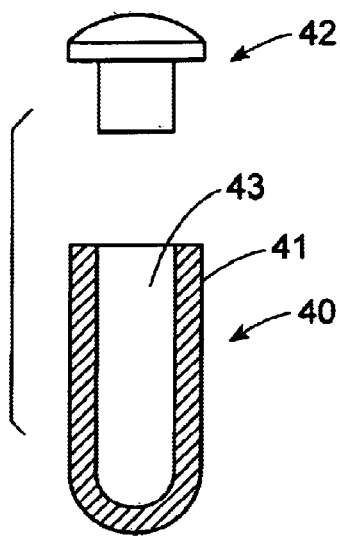
FIG. 4 is a longitudinal cross-sectional view of an implantable drug delivery device comprising a sealable capsule in accordance with another embodiment of the present invention.

It is to be understood that any of the solid embodiments illustrated hereinabove may be hollowed out to increase the surface area of the device in contact with body fluids and tissue and increase the rate of release of a therapeutic agent therefrom. A capped tubular embodiment 30 of the device is shown in exploded elevational view in FIG. 3. The tubular body portion 31 of the device 30 comprises a plurality of tubular embodiments 10i adhered to one another. The open ends of the body portion 31 are sealed with caps 32 to provide a chamber 33 therewithin. Similarly, the capsular embodiment 10b of the drug delivery device can comprise a fillable device as shown in FIG. 4. The hollow capsular embodiment 40 of a drug delivery device in accordance with the present invention includes a cylindrical, biodegradable body 41 and a cap 42. The biodegradable II polymeric material comprising the body 41 and cap 42 may include a first therapeutic agent incorporated therein which is slowly released during biodegradation of the body. The capsular embodiment 40 further includes a chamber 43 therewithin into which a second therapeutic agent may be placed for dispensation after the body has biodegraded. In embodiments 30 and 40, both the polymeric composition comprising the body portion or the chamber may include a therapeutic agent therewithin.

Figure 5:
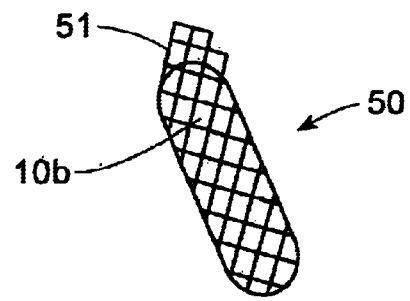
FIG. 5 is a perspective view of a capsular drug delivery module disposed within an implantable mesh bag.

It may be desirable to employ any of the foregoing embodiments of a modular drug delivery device for the controlled, localized release of a therapeutic agent to soft tissue. Any of the above-described modular drug delivery devices, either alone or in combination, can be placed in a mesh or porous container for implantation within the body as shown at numeral 50 in FIG. 5. FIG. 5 is a perspective view of a capsular drug delivery module 10b disposed within an implantable mesh bag 51. Other geometries of drug delivery modules such as one or more spherical beads may also be placed within the mesh bag prior to implantation. The mesh may comprise a durable (i.e., nonbiodegradable), biocompatible material such as Dacron® (manufactured by Invista North America S.A.R.I. Corporation), yarns of synthetic fibers, and synthetic fibers and filaments for use in the manufacture of fabrics and textiles or Gortex®(manufactured by W.L. Gore & Associates, Inc.), fabrics with polytetrafluoroethylene laminate or it may, comprise a less durable, biocompatible, biodegradable polymer. If a biodegradable polymer is used to fabricate the mesh, the polymer or copolymer should be selected to persist until the module(s) contained therewithin are biodegraded. The mesh bag 51 provides attachment means for suturing the device to a soft tissue or bone fastener in order to securely position the device 50 adjacent a targeted release site during biodegradation thereof and release of the therapeutic agent contained therewithin.

Various methods for forming bioabsorbable polymer-therapeutic agent composites are known in the art. For example, U.S. Pat. Nos. 5,268,178 and 5,681,873 disclose methods for making such composites. A first method for making implantable modular drug delivery devices is to dissolve a selected biodegradable polymer, such as polylactic acid, preferably obtained in the form of a powder, in a ketone solvent such as acetone or hexafluoropropanone. After the polymer has dissolved, the therapeutic agent is added in the desired proportion, and the solution is dried to form a thin layer. These steps are repeated, forming a multiple layer, laminate material comprised of the biodegradable polymer and the therapeutic agent. The laminate material can then be molded, extruded or compressed into a desired shape, such as a cylinder, tube or an annular disk, to provide a shaped module. The shaped module may be hardened by dipping it in acetone and drying it until it is hard. It is also desirable to sterilize the implant with electron beam or gamma radiation before placing it in a receiving recess in a prosthesis prior to implantation.

In another method, the bioabsorbable polymer and one or more crystallization-controlling agent, and/or other additives, as desired, are compounded by melting the polymer and combining the other ingredients of the formulation with the molten polymer. The crystallization-controlling agent, and/or other additives, may be added to the molten polymer. The melting temperature for a particular bioabsorbable polymer will vary with the molecular weight and/or the structure of the polymer, which information is known in the art. It is preferred that a suitable polymer for compounding by this method have a melting temperature less than 100° C. A polymer having a lower melting temperature will have a higher viscosity, which aids in keeping certain ingredients suspended in the mix.

The molten mixture is cooled or annealed under controlled conditions to achieve the desired physical properties for the composition, namely, moldable and cohesive. The cooling or annealing temperature is preferably about 10° C. below the melting temperature, and the cooling or annealing time is about 1–72 hours, preferably about 12–24 hours. The composition is then allowed to cool to room temperature. Properly mixed and cooled or annealed compositions are characterized as being cohesive with a uniform, or homogenous consistency throughout its mass. Homogeneity of the physical properties of the composition requires a substantially uniform distribution of crystalline regions of polymer throughout the composition. The overall amount of crystallinity, the number and size of the crystalline regions plus the degree of order in the crystalline regions will also affect the physical properties of the composition.

The therapeutic agent may be added to the composition during the compounding process while the polymer, and optional crystallization-controlling agents are in a molten state, while the composition is cooling, or after the composition has cooled. If the bioactive agent is added after the composition has cooled, it may be incorporated into the composition by kneading the biologically-active agent and cooled composition together. Once the composition is placed into the prosthesis and the prosthesis implanted within the body, the biologically-active agent is released into the adjacent tissue fluids, preferably at a controlled rate.

The release of the biologically-active agent from the matrix of the composition may be varied, for example, by the solubility of the biologically-active agent in aqueous tissue fluids, the distribution of the bioactive agent within the matrix, the size, shape, porosity, solubility and biodegradability of the composition, the type and amount of crystallization-controlling agent and/or an additive, and the like. The relative amounts of bioabsorbable/biodegradable polymer in the implantable modular drug delivery device in accordance with all of the embodiments of the present invention may vary widely, depending on the rate of dissolution of the polymer (and, therefore, the rate of drug release) desired. The polymer composition includes the therapeutic agent in an amount effective to provide the desired level of biological, physiological, pharmacological and/or therapeutic effect in the animal. There is generally no critical upper limit on the amount of the therapeutic agent included in the composition. The only limitation is a physical limitation for advantageous application (i.e., the therapeutic agent should not be present in such a high concentration that the consistency and handling of the composition is adversely affected). The lower limit of the amount of therapeutic agent incorporated into the composition will depend on the activity of the therapeutic agent and the period of time desired for treatment.

A variety of antibiotic drugs can be used in the implants to treat or prevent infection. Suitable antibiotics include many classes, such as aminoglycosides, penicillins, semi-synthetic penicillins, cephalosporins, doxycycline, gentamicin, bacitracin, vancomycin, methicillin, cefazolin and quinolines. Clindamycin has been reported to release readily from composites comprising polylactic acid. Anti-inflammatory agents such as hydrocortisone, prednisone, and the like may comprise the therapeutic agent. Substances useful for promoting growth and survival of cells and tissues or augmenting the functioning of cells, as for example, a nerve growth promoting substance such as a ganglioside, a nerve growth factor; a hard tissue growth promoting agent such as an osteoinductive growth factor, are also possible therapeutic agents suitable for incorporation within a modular drug delivery device of the present invention. The protein lactoferrin, an iron scavenger, has recently been shown to prevent the buildup of "biofilms" comprising bacterial colonies. The incorporation of lactoferrin into an implantable modular drug delivery system may be useful for preventing the formation of harmful biofilms at a surgical site.

The weight ratio of biodegradable material to antibiotic is preferably between about 50:1 and about 5:1, and is most preferably about 10:1. Other pharmaceutically acceptable drugs, additives, or excipients can also be included in the implantable modular drug delivery devices. The modular drug delivery devices are preferably shaped to be received within a mating recess in an implantable prosthesis, thereafter to be affixed to the prosthesis and become integral therewith. The affixation means can be an adhesive such as methylmethacrylate or the drug delivery device can be threaded and screwed into a tapped hole within a prosthesis.

The rate of release of a therapeutic agent from the modular drug delivery device generally depends on the concentration of the therapeutic agent in the composition and the choice of bioabsorbable polymer. For a particular polymer, the rate of release may further be controlled by the inclusion of one or more additives that function as a release rate modification agent, and by varying the concentration of that additive. The release rate modification additive may be, for example, an organic substance which is water-soluble or water insoluble. Useful release rate modification agents include, for example, fatty acids, triglycerides, other like hydrophobic compounds, organic solvents, and plasticizing compounds.

While particular embodiments of the present invention have been illustrated and described, it would be obvious to those skilled in the art that various other changes and modifications can be made without departing from the spirit and scope of the invention. For example, any of the solid embodiments discussed herein can include a cavity therewithin that may contain a therapeutic agent. Similarly, different modules of the solid, modular drug delivery devices such as, for example, the disk embodiment 10c, may contain different therapeutic agents and/or comprise different polymer blends offering different biodegradation rates and be attached to one another to form a composite device. It is therefore intended to cover in the appended claims all such changes and modifications that are within the scope of this invention.

We claim:

1. An implantable prosthetic device having a surface contour, and comprising a solid modular implantable drug delivery device within a shaped recess within the outer surface of an implantable prosthesis, said device being operable for releasing a therapeutic agent into the body of an animal following implantation of the prosthesis within the body of the animal, the device comprising:

(a) solid module comprising a biodegradable polymer dimensioned to fit snugly within the shaped recess in the prosthesis; and (b) a therapeutic agent that is released into the body of the animal during biodegration of said biodegradable polymer over a predefined dosing period.

2. The device of claim 1 wherein when said solid module comprising a biodegradable polymer is received within the shaped recess of the implantable prosthesis, the contour of the outer surface of the prosthesis is not substantially altered.

3. The device of claim 1 wherein said solid module comprising a biodegradable polymer is affixed to said prosthesis.

4. The device of claim 2 wherein said solid module comprising a biodegradable polymer is affixed to said prosthesis.

5. The device of claim 1 wherein said therapeutic agent is contained within a cavity in said solid module.

6. The device of claim 2 wherein said therapeutic agent is contained within a cavity in said solid module.

7. The device of claim 1 comprising a plurality of solid modules.

8. The device of claim 7 wherein said plurality of solid modules are affixed to one another.

9. The implantable prosthetic device of claim 1 comprising: (a) a mesh container;

and (b) at least one solid module comprising a biodegradable polymer and a therapeutic agent contained within, said mesh container.

10. The implantable prosthetic device of claim 1 wherein the prosthesis is a femoral pin.

11. The implantable prosthetic device of claim 1 wherein the prosthesis is a bone plate.

12. The implantable prosthetic device of claim 11, wherein the solid module is shaped like a rectangular tile, and the recess is a mating receptacle therefor.

13. The implantable prosthetic device of claim 1 wherein the recess is formed by drilling a hole in the prosthesis.

14. The implantable prosthetic device of claim 1, wherein the solid module is shaped like a rod, and is placed, within a cylindrical recess in the prosthesis.

15. The implantable prosthetic device of claim 7, wherein one of the solid modules is hollowed out to increase the surface area in contact with the body fluids, and increase the rate of release of a therapeutic agent therefrom.

16. The implantable prosthetic device of claim 1, wherein the solid module is shaped like a tapered conical plug.

17. The implantable prosthetic device of claim 1, wherein the solid module is shaped like a threaded cylindrical plug.

18. The implantable prosthetic device of claim 7, wherein the modules comprise a plurality of stacked disks.

19. The implantable prosthetic device of claim 1, wherein the solid module is shaped like a capped tub.

20. A method for controlled phased release of a therapeutic agent into an orthopedic surgical site, comprising providing an implantable prosthesis, forming at least one shaped solid modular drug delivery device comprising a biodegradable polymer and a therapeutic agent, forming a recess in the surface of the prosthesis shaped to receive the shaped solid modular drug delivery device, placing at least one shaped solid modular drug delivery device in the recess, and implanting the prosthesis in the body of an animal.

* * * * *